(12) United States Patent
Jelinek

(10) Patent No.: US 8,008,039 B2
(45) Date of Patent: Aug. 30, 2011

(54) POLYDIACETYLENE-CONTAINING SOLID COLORIMETRIC AND /OR FLUORESCENT DETECTOR, METHOD FOR ITS PREPARATION AND USES THEREOF

(76) Inventor: Raz Jelinek, Reut (IL)

( * ) Notice: Subject to any disclaimer, the term of this patent is extended or adjusted under 35 U.S.C. 154(b) by 693 days.

(21) Appl. No.: 11/795,499

(22) PCT Filed: Jan. 19, 2006

(86) PCT No.: PCT/IL2006/000078
§ 371 (c)(1),
(2), (4) Date: Jan. 7, 2008

(87) PCT Pub. No.: WO2006/077586
PCT Pub. Date: Jul. 27, 2006

(65) Prior Publication Data
US 2008/0293095 A1 Nov. 27, 2008

Related U.S. Application Data

(60) Provisional application No. 60/644,700, filed on Jan. 19, 2005.

(51) Int. Cl.
*C12Q 1/04* (2006.01)
*C12Q 1/06* (2006.01)
(52) U.S. Cl. ........................ 435/34; 435/288.7
(58) Field of Classification Search ............... 435/34, 435/288.7
See application file for complete search history.

(56) References Cited

U.S. PATENT DOCUMENTS 6,022,748 A * 2/2000 Charych et al. ............... 436/527
6,361,962 B1 3/2002 Lentini et al.

FOREIGN PATENT DOCUMENTS

| WO | WO 97/27316 | 7/1997 |
| WO | WO 98/39632 | 9/1998 |
| WO | WO 00/55623 | 9/2000 |
| WO | WO 2005/005982 | 1/2005 |

OTHER PUBLICATIONS

Jelinek R et al.: "Interfacial Catalysis by Phospholipases at Conjugated Lipid Vesicles: Colorimetric Detection and NMR Spectroscop", Chemistry and Biology, Current Biology, London, GB, vol. 5, Nov. 1998, pp. 619-629.
Jelinek R et al.: "Polymerized Lipid Vesicles as Colorimetric Biosensors for Biotechnological Applications", Biotechnology Advances, Elsevier Publishing, Barking, GB, vol. 19 (2), 1 Apr. 2001, pp. 109-118.
Rozner S et al.: "Detection and Analysis of Membrane Interactions by a Biometic Colorimetric Lipid/Polydiacetylene Assay", Analytical Biotechnology, Academic Press, San Diego, CA, US, vol. 319 (1), Aug. 1, 2003, pp. 96-104.
Pan J. J. et Charych D.: "Molecular recognition and Colorimetric Detection of Cholera Toxin by Poly(acetylene) liposomes incorporating Gm1 ganglioside", Langmuir, vol. 13, 1997, pp. 1365-1367.

* cited by examiner

*Primary Examiner* — Chih-Min Kam
(74) *Attorney, Agent, or Firm* — Nixon & Vanderhye P.C.

(57) ABSTRACT

A colorimetric and/or fluorescent detector, which comprises a film of polydiacetylenes and lipids deposited on a substrate, wherein said film is coated with one or more layers, wherein at least one of said layers is capable of supporting the growth of microorganisms. Also provided are processes for preparing the novel colorimetric and/or fluorescent detector and uses thereof in the detection of bacteria.

2 Claims, 1 Drawing Sheet

POLYDIACETYLENE-CONTAINING SOLID COLORIMETRIC AND /OR FLUORESCENT DETECTOR, METHOD FOR ITS PREPARATION AND USES THEREOF

This application is the U.S. National Phase of international application PCT/IL2006/000078 filed 19 Jan. 2006, which designated the U.S. and claims the benefit of U.S. Provisional Application No. 60/644,700 filed 19 Jan. 2005, the entire contents of each of which are hereby incorporated by reference.

Polydiacetylenes (a class of polymers obtained by the polymerization of diacetylene monomers) are known to display a readily visible blue to red color transition in response to a variety of perturbations. Polydiacetylenes were thus incorporated in different types of detectors and biosensors intended for various applications.

A colorimetric and/or fluorescent detector, which is based on the combination of polydiacetylenes (hereinafter sometimes abbreviated "PDA") and lipids incorporated together within an organic matrix made by a gel material that is capable of supporting the growth of microorganisms (e.g., nutrient agar), was recently disclosed in WO 2005/005982.

According to the preparative examples of WO 2005/005982, the lipids and the polymerized diacetylenes are assembled in the form of vesicles or liposomes. The organic matrix described in WO 2005/005982 is obtained by suspending the diacetylene monomers and the lipids in an aqueous medium, sonicating the suspension and mixing the same with a sterilized suspension of a gel-forming material and nutrients. The resulting mixture is allowed to solidify and the diacetylene monomers are subsequently polymerized (by means of ultraviolet radiation) to form the blue organic matrix suitable for use as a colorimetric and/or fluorescent detector. Alternatively, the monomers and lipids—containing suspension may be polymerized before it is mixed with the suspension of a gel-forming material and nutrients. In any case, a hot liquid mixture containing lipids, polydiacetylenes (or their monomer precursors) and the gel forming material is allowed to solidify within the confine of a suitable vessel (e.g., in a Petri dish) or as a film. The latter option was accomplished according to the description of WO 2005/005982 by placing a drop of the aforementioned liquid composition onto the surface of a first glass slide, and covering the same with a second glass slide, in order to flatten the drop into a film on the surface of the first glass slide. The detector disclosed in WO 2005/005982 responds to the presence of bacteria in a tested sample that is contacted therewith by undergoing a readily visible blue to red color change and by generating a characteristic fluorescence emission spectrum, after a relatively short incubation period of said bacterial species.

The present invention relates to a novel colorimetric and/or fluorescent detector, which comprises a film of polydiacetylenes and lipids deposited on a substrate, wherein said film is coated with one or more layers, wherein at least one of said layers is capable of supporting the growth of microorganisms.

By the term "colorimetric and/or fluorescent detector" is meant that the construct described immediately hereinabove is capable of responding to the presence of various analytes, and especially bacteria, by exhibiting a chromatic transition (e.g. a change in visible color of the film or a portion thereof) and/or a characteristic fluorescent emission associated therewith.

The colorimetric and/or fluorescent detector according to the present invention comprises two components, namely, a first component, which is a film of polydiacetyelenes and lipids, and a second component, which is a coating containing one or more layers applied onto the film, which components are most conveniently prepared separately and are finally coupled to one another. The term "substrate", as used herein, means to indicate a suitable support, onto which the film containing the polydiacetyelenes and the lipids is deposited.

The first component, which constitutes the chromatic detecting element, is provided in the form of polydiacetylenes and lipids-containing film deposited on a suitable substrate. Most preferably, the polydiacetylenes and the lipids are arranged in the film according to the present invention in interspersed (or intertwined) planar sheets comprising monolayer and multilayer structures. The structure of the polydiacetylenes and lipids containing film provided by the present invention is discussed in more detail below.

Preferred diacetylene monomers that may be used according to the present invention for preparing the chromatic polydiacetylenes are well known in the art and are described, inter alia, in WO 99/10743 and US 2002/0034475, which are incorporated herein by reference. Most preferably, the diacetylene monomers are selected from the group consisting of 10,12-tricosadiynoic acid, 10,12-pentacosadiynoic acid, 10,12-octadecadiynoic acid, 5,7-docosadiynoic acid, 5,7-pentacosadiynoic acid and 5,7-tetracosadiynoic acid. These monomers are all commercially available.

Preferred lipids that may be used according to the present invention include, but are not limited to, glycolipids, phospholipids, lipopolysaccharides, steroids and alcohol derivatives thereof, extracts of lipids of the cell membrane obtained from various microorganisms as well as other components of the cell membrane. Particularly preferred lipids are selected from the group consisting of dimyristoylphosphatidylcholine (hereinafter abbreviated DMPC), phosphatidylglycerol (hereinafter abbreviated PG) dipalmitoylphosphatidylcholine (hereinafter abbreviated DPPC), natural phosphatidylcholine (hereinafter abbreviated PC), dimirystoylphosphatidylethanolamine (hereinafter abbreviated DMPE), cardiolipin, dimyristoylphosphatidylserine (hereinafter abbreviated DMPS), sphingomyelin, sphingolipids, ceramide, galactosylceramide, and cholesterol, or mixtures thereof.

The film according to the present invention is prepared by dissolving the diacetylene monomer and the lipids in a suitable organic solvent, which is most preferably chloroform, or mixtures thereof with other, readily volatile, organic solvents. The molar ratio between the diacetylene monomers and the lipids in the resulting solution is generally in the range of 95:5 and 3:2. The formation of the film may then be accomplished by means of various film-forming methods, and most preferably, by employing the Langmuir-Blodgett technique, or a modified version of said technique. Briefly, the solution containing the diacetylene monomers and the lipid molecules is spread onto the air/water interface of a Langmuir trough, (preferably between 50 µL and 200 µL solution in a 300 cm² trough). The organic solvent is allowed to evaporate, following which the film is compressed to a pressure in the range of 10 to 20 mN/m, wherein the controlled compression of the film is carried out by movable barrier means which are suspended within the Langmuir through and are capable of exerting a lateral pressure onto a layer of the diacetylenes and lipid molecules on the surface of the water. The speed of the movable barrier means is typically adjusted to a value in the range of 10 to 20 cm²/sec, in accordance with the specific film depositing apparatus used.

The compressed film containing the diacetylenes and the lipids is then transferred onto the surface of a suitable substrate, which is preferably made of a transparent solid such as glass, or non-transparent substrates such as silicon or metals. The surface of the substrate may be hydrophobized before the film is deposited thereon. To this end, the surface of the substrate is pre-treated with a suitable cleaning solution, washed with water and dried, following which the substrate (e.g., a glass slide) is coated with octadecyltriethoxysilane by procedures well known in the art. However, pre-covering the surface of the substrate with octadecyltriethoxysilane is not mandatory, and substrates having hydrophilic character may also be used according to the present invention.

The compressed film which contains the diacetylenes and the lipids is most conveniently transferred from the water/air interface of the Langmuir trough onto the surface of the substrate by use of the horizontal-touch Langmuir-Schaefer technique, according to which said substrate is horizontally touched to the water surface, removed therefrom and dried in open air. This procedure is repeated several times, preferably between 3 to 6 times, in order to transfer sufficient quantity of the film from the Langmuir trough onto the substrate. Between each repetition, the film remaining in the Langmuir trough is allowed to equilibrate, reaching a pressure value which is slightly below the pressure measured for the preceding film.

Having completed the successive loading of the film onto the substrate, the film deposited on the surface of the substrate is irradiated by means of UV-radiation at 254 nm, typically for about 2 minutes using a UV crosslinker, in order to effect the polymerization of the diacetylene monomers contained therein, whereby a blue polydiacetylenes and lipids-containing film is obtained. It should be noted that the polymerization step may be carried out while the film is still in the Langmuir trough, following which the polymerized film is transferred onto the substrate. It has been observed, however, that more pronounced chromatic signals are obtained when the polymerization step is performed after the film has been transferred to the substrate. According to another embodiment, the polymerization of the diacetylene monomers is carried out after the film has been transferred to the substrate and has been coated, as will be described below.

Although the Langmuir-Blodget (or the Langmuir-Schaefer) methods represent the preferred techniques by which the film according to the present invention is prepared, it should be noted that alternative film-forming methods may be also applied according to the present invention, including a spin-coating process, wherein a solution of the diacetylene monomers and the lipids in an organic solvent at concentrations between 20-100 mM is poured or sprayed onto a suitable substrate (e.g., a glass slide), following which the substrate is rotated at a constant rate for a sufficient period to give the film-covered substrate. This procedure, followed by drying, is also illustrated in the Examples below.

The second component of the color and/or fluorescent detector according to the present invention is a coating which comprises one or more layers applied onto the film that was deposited on the substrate, as described above, wherein at least one of said layers is capable of supporting the growth of microorganisms. Preferably, the coating comprises a single layer, namely, the layer which is capable of supporting the growth of microorganisms is directly applied onto the film and constitutes the outer layer of the detector.

The coating comprises a material which is suitable for the growth of microorganisms. The coating thus comprises polymers that are capable of forming gel-like solid at room temperature, the melting point of said polymers being preferably below 35° C., and more preferably below 30° C. Particularly preferred polymers useful for forming the coating according to the present invention are selected from the group consisting of polysaccharides and polyacrylamides. More specifically, the coating applied onto the film of the present invention is in the form of a thin layer comprising agar, agarose and other natural or synthetic gelatinous polymers, wherein nutrients required for the growth of microorganism are optionally present in said coating. Most preferably, the film according to the present invention is coated with an agarose layer.

In practice, the coating layer is prepared by forming a liquid suspension of the gel-forming material (e.g., agar, agarose), and mixing the same with the bacterial growth medium. The growth medium is most suitably LB (Luria-Bertani) growth medium optionally supplemented with standard bacteriological additives, for example, yeast extract, peptide mixtures, amino acids and the like. The liquid suspension is subjected to sterilization and is subsequently spread over the surface of the film (the temperature of the liquid suspension at this stage is about 30° C.), to form a substantially uniform coating thereon, the thickness of which is in the range between 0.05 and 5 mm, although thinner coatings may be also prepared, if desired. The coating is allowed to solidify on the film, and the resulting construct may be subjected to a first polymerization (in the event that the diacetylene monomers were not polymerized during the preceding stages) under the conditions described above, or to a second polymerization.

Accordingly, in another aspect, the present invention provides a process for preparing colorimetric and/or fluorescent detector, which comprises depositing a film of diacetylenes and lipids on a substrate, polymerizing the diacetylene monomers and coating said film with one or more coating layers, wherein at least one of said layers is made of a material which is capable of supporting the growth of microorganism. Alternatively, there is provided a process for preparing colorimetric and/or fluorescent detector, which comprises depositing a film of diacetylenes and lipids on a substrate, coating said film with one or more coating layers, wherein at least one of said layers is made of a material which is capable of supporting the growth of microorganism, and polymerizing the diacetylene monomers.

The polydiacetylene and lipids-containing film, which is provided with a thin coating layer that is capable of supporting the growth of microorganisms, exhibits blue color and may be easily and conveniently applied for rapidly detecting the presence of various analytes that are capable of interacting with cellular membranes, as described in WO 2005/005982, which is incorporated herein entirely by reference. It should be noted the coating of the film, which comprises one or more layers, wherein at least one of said layers is capable of supporting the growth of microorganisms, also performs a "filtering" role—preventing external substances from reaching the lipids/polydiacetylene detector film and inducing undesired chromatic transitions.

Accordingly, in another aspect, the present invention provides a method for detecting the presence of an analyte in a sample, comprising contacting the sample to be tested with a film of polydiacetyelenes and lipids deposited on a substrate, wherein said film is coated with a layer which is capable of supporting the growth of microorganisms, and following a suitable incubation period, either observing the color of said coated film or the fluorescence emission thereof, wherein a change in said color (typically a blue to red transition) or a characteristic fluorescence emission (typically the emission at about 560 or 650 nm, following excitation at about 485-500 nm) indicate the presence of said analyte in the tested sample.

In general, it is sufficient to place the sample to be tested on the surface of the coated film, and following a suitable incubation period, which depends on the type of the analyte, observing the color of said coated film or the fluorescence emission thereof, wherein a change in said color and/or a characteristic fluorescence emission indicate the presence of said analyte in the tested sample. One preferred embodiment of the invention relates to the detection of microorganisms and/or toxins produced thereby. The microorganisms that may be detected by the method according to the present invention include, inter alia, bacteria and fungi. Typical incubation time may vary between 1 to 13 hours. It is to be emphasized that, in the case of bacterial contamination, the blue to red color transition may be observable even when no bacterial colonies are visible on the coated film.

The blue to red transition exhibited by the coated film of the present invention can be observed by the naked eye. Alternatively, the color changes may be recorded by means of UV-vis spectrophotometer or an ELISA plate reader. Typically, the spectrophotometric reading is made at 27° C. using a 1 cm optical path cell with a standard laboratory spectrophotometric device. The blue-to-red chromatic transitions may be quantified using the chromatic response factor, as defined below:

$$\% \ CR = \frac{PB_0 - PB_1}{PB_0} \times 100,$$

$$\text{where } PB = \frac{A_{blue}}{A_{blue} + A_{red}},$$

where $A_{blue}$ and $A_{red}$ are the absorbance measured at about 640 nm and about 500 nm, respectively. $PB_0$ is the blue/red ratio of the coated film before induction of color change, and $PB_1$ is the value obtained after adding the tested sample thereto.

Alternatively, the detection methods provided by the present invention may be based on the characteristic fluorescent emission associated with the changes in the coated film that occur in response to the presence of the analyte. Detection of this fluorescent emission may be accomplished by illuminating the surface of the coated film with a suitable light source emitting light at about 485-500 nm. The appearance of characteristic maxima at about 560 and/or 650 nm in the fluorescence spectrum obtained following said excitation serves as an indication for the presence of the tested analyte. The aforementioned procedure may be suitably carried out using an inverted microscope fitted with fluorescent excitation and detection means, or a standard fluorescence spectrophotometer.

The colorimetric and/or fluorescent detector provided by the present invention, which comprises a film of polydiacetyelenes and lipids deposited on a substrate, wherein said film is coated with a thin layer which is capable of supporting the growth of microorganism, is especially suitable for detecting the presence of bacteria in samples of body fluids, such as urine, blood and spinal cord fluid. Thus, the urine sample or the blood sample to be tested is placed on the surface of the coated film, and following a suitable incubation period at about 35° C. to 37° C., a visible blue to red color change of said coated film, or the detection of a characteristic fluorescence emission, indicate the presence of bacteria in the tested sample.

In another embodiment, water samples (e.g., of clean water, treated water and sewage) may be contacted with the coated film of the present invention, in order to determine the presence of microorganisms in the tested water sample.

In another embodiment of the present invention, the method disclosed and described herein is used to detect the presence of microorganisms and/or their toxins in food products. In one mode of operation, samples of either the solid food product (e.g. meat, hard cheese, etc.) or liquid food product (e.g. milk or juice) are streaked onto the surface of the coated film, and following a suitable incubation period at about 35° C. to 37° C., a visible blue to red color change of said coated film, or the detection of a characteristic fluorescence emission, indicate the presence of bacteria in the tested food sample.

It should be noted that despite the fact that in many cases bacterial colonies may be observed on the surface of coated film only after a relatively long incubation period (for example, actual visible colonies of *E. coli* JM101 and *Salmonella typhimurium* appear following an incubation period of approximately ten hours at 35° C.), it is possible to determine the presence of bacteria in the tested sample by contacting the same with the coated film and following an incubation period that is less than the period of time required for the development of visible bacterial colonies, producing the blue-red transitions or fluorescent areas within said coated film (observed visibly, or by using an ELISA fluorescence reader, wherein the excitation is at 495 nm and the emission is at 560 nm), thereby readily confirming the presence of the bacteria in the tested sample. For the specific bacterial species mentioned above, an incubation period of about three hours was found sufficient.

It should be noted that the coated film provided by the present invention may be incorporated into the packaging of the material to be tested (e.g., packaging of food products; blood bags, as used for example in connection with blood donation). In this way, it is possible to continuously monitor the quality of the tested material and to timely detect possible deterioration thereof due to, for example, microbial contamination, by means of a distinct blue-to-red color change of the packaging. In order to enhance readability, the abovementioned coated film may be spatially arranged within the food packaging such that upon changing color, a distinct symbol or word becomes visible. Thus, if the coated film of the present invention were to be incorporated in the form of the letter 'X' in a portion of the packaging having exactly the same color as the coated film, microbial contamination of the food product would be indicated by the presence of a red letter 'X' set in a blue background.

In another aspect, the present invention relates to a colorimetric and/or fluorescent detector, which comprises a film of polydiacetyelenes and lipids deposited on a substrate, wherein said film is coated with one or more layers, wherein at least one of said layers is capable of supporting the growth of microorganisms, and wherein at least one compound exhibiting antibacterial activity is included in said coating layer(s). The inclusion of an antibiotic compound within the coating of the film of the present invention is suitably carried out by dissolving or suspending said antibiotic compound in the liquid suspension of the gel-forming material (e.g., agar, agarose) before the application of said liquid suspension onto the surface of the film to produce the coating thereon. The concentration of the antibiotic compound in the said liquid mixture is in the range of 1-50 μg/ml.

Bacterial strains that are resistant to the specific antibiotic compound incorporated in the coating of the film (or mutants in which resistance was added through genetic engineering), will be able to grow in the coated film of the present invention, and induce the chromatic change, or the characteristic fluorescence emission described above.

For example, the growth of *salmonella typhimurium* wild type, kanamycin-resistant *salmonella typhimurium* and *E. Coli* MC4100 strain in the coated film of the present invention induces a visible color change from blue to red, or the characteristic fluorescence emission. However, when the coated film further comprises the antibiotic compound kanamycin, the blue to red color transition, or the characteristic fluorescence emission, will be observed for a coated film that has been contacted with kanamycin-resistant *salmonella*, but not for a coated film that has been contacted with the other two bacterial species mentioned above. On the other hand, the inclusion of streptomycin in the coated films of the present invention will prevent the blue to red color change (or the corresponding characteristic fluorescence emission) in the case of *salmonella typhimurium* wild type and kanamycin-resistant *salmonella typhimurium*, but not in the case of *E. Coli* MC4100 which is resistant to streptomycin.

Thus, in another aspect, the present invention provides a method for determining the antibiotic resistance of bacterial strain, which comprises contacting the bacterial strain to be tested with a film of polydiacetyelenes and lipids deposited on a substrate, wherein said film is coated with a thin layer which is capable of supporting the growth of microorganism, wherein at least one compound exhibiting antibacterial activity is included in said coating layer, and following a suitable incubation period, either observing the color of said film or detecting a fluorescent emission thereof, wherein a change in said color or a characteristic fluorescence emission indicate that said bacterial strain is resistant to said antibiotic agent. Similarly, the incorporation of different antibiotic substances in the coating could facilitate differentiation and identification of bacteria in tested sample through determination of their antibiotic resistance profile.

A film containing polydiacetylenes and lipids, deposited according to the procedure described above onto a glass slide covered with octadecyltriethoxysilane, was investigated by means of atomic force microscopy (AFM). AFM measurements were performed at ambient conditions using a Thermomicroscopes CP Research Instrument mounted on an active antivibration table. A 100 μm scanner was used. Microfabricated Si oxide ultralevers (Thermomicro) with integrated pyramidal tips were used. The 512 pixel×512 pixel images were taken in a tapping mode with a scan size from 1 μm, at a scan rate of 1 Hz.

FIG. 1*a* shows an AFM image of the film deposited on the glass slide, and FIG. 1*b* illustrates the height profile of the film (assuming a Cartesian coordinate system XYZ, wherein the glass slide defines the XY plane, the ordinate in the graph shown in FIG. 1*b* corresponds to the height of the film, and is accordingly designated as the Z axis). The film deposited onto the glass slide comprises a multilayer domain of the polydiacetylenes (and specifically, a trilayer domain, since the measured height of the domain, which is about 9 nm, corresponds to a trilayer structure of polydiacetylenes) and a monolayer domain of the lipids, with a measured height of about 4 nm.

EXAMPLES

Example 1

Figure 1A:
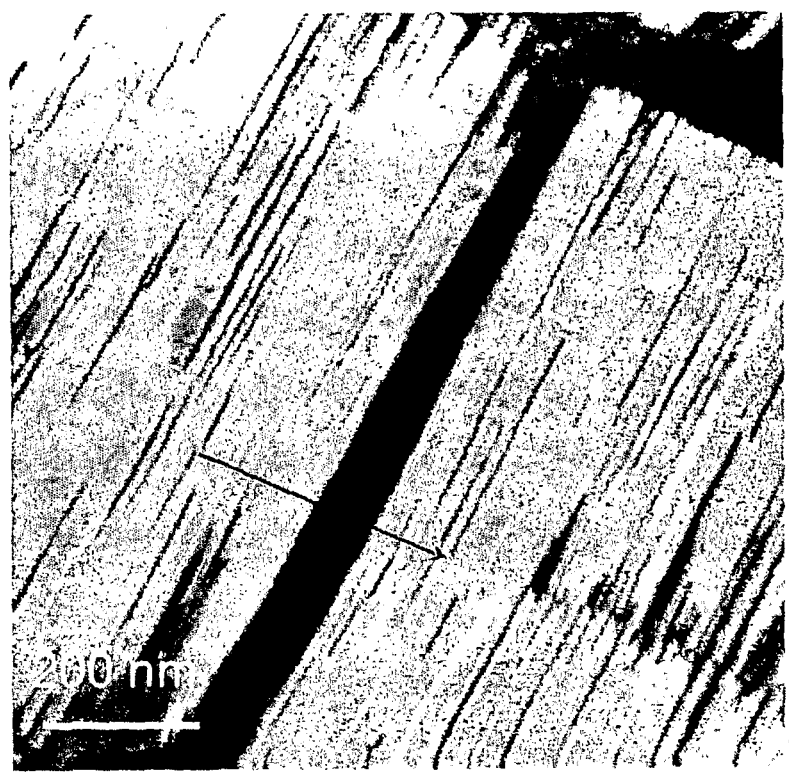
FIGS. 1*a* and 1*b* are AFM image of the film deposited on the glass slide, and the height (or thickness) profile thereof, respectively.
Figure 1B:
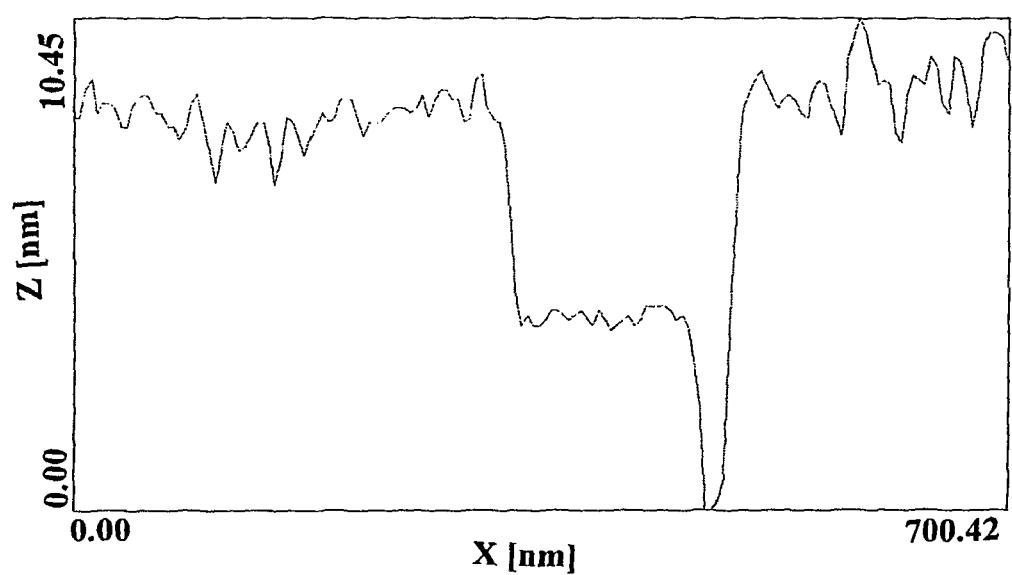

Preparation of a Langmuir-Blodget Film of Polydiacetylenes and Lipids Having an Agarose Coating Thereon Glass Substrate
Glass slides were dipped in a cleaning (piranha) solution consisting of 70 ml of sulfuric acid and 30 ml of hydrogen peroxide for 30 minutes at 70° C. This was followed by sonication in the same solution for 10 minutes. The glass slides were then rinsed thoroughly with pure water, dried at 70° C. and then immersed in a cyclohexane solution (100 ml) containing 300 μl of octadecyltriethoxysilane (OTS) for 12 hours. The glass slides were finally washed with cyclohexane to remove residual non-covalently bound OTS molecules.
Deposition of the Film onto the Glass Substrate
34.6 mg of 10,12-tricosadiynoic acid (abbreviated TRCDA; purchased from GFS chemicals, Powell, Ohio) were dissolved in a vessel containing 5 ml of chloroform, to form a first stock solution in a concentration of 20 mM. 67.8 mg of DMPC (Sigma-Aldrich) were dissolved in a separate vessel containing 5 ml of chloroform, to form a second stock solution in a concentration of 20 mM. Aliquots of 1.0 ml of DMPC and 9.0 ml of TRCDA were taken from each of the two stock solutions and were mixed to form a stock solution in which the molar ratio between the monomer and the lipid was 9:1.

The resulting stock solution was spread onto the air/water interface of a computerized Langmuir through (manufactured by Nima Technology Ltd., Model 622/D1), until a surface pressure of about 3 to 4 mN/meter was measured (the pressure applied to the TRCDA/DMPC layer was monitored using a 1 cm width filter paper (Wilhelmy plate). The volume added was 50 μL in a 300 $cm^2$ trough. The evaporation of the chloroform was completed at room temperature after 15 minutes, following which the film was compressed at a constant barrier speed in the range of 8 to 12 $cm^2$/min. When the surface pressure measured was about 14 to 17 mN/m, the compression was stopped. The resulting film was allowed to equilibrate for 10 minutes at a constant surface pressure.

The film was then transferred onto the hydrophobized surface of the treated glass slides by means of the horizontal touch method (the Langmuir-Schaefer technique). This step was repeated 3-4 times. Before each transfer, the film remaining in the trough is allowed to equilibrate before portions thereof are transferred onto the glass slide. The glass slide was dried in open air after each film deposition step.

Finally, the film deposited on the glass slide was UV-irradiated at 254 nm for two minutes using a UV cross linker (Stratagene) to polymerize the TRCDA monomers, and to form a blue-colored film.
Agarose Coating
To LB (Luria-Bertani) growth medium was added a solution of agarose (Conda SA) in water (1% w/v). The resulting mixture was sterilized for 20 minutes and allowed to cool to slightly below 30° C. The liquid mixture was then spread onto the polydiacetylenes-and-lipids-containing blue film to form a thin coating thereon, such that the thickness of the coating is about 1 mm. The agarose coating was then allowed to solidify.

Example 2

Preparation of a Spin-Dried Film of Polydiacetylenes and Lipids Having an Agarose Coating Thereon Glass Substrate
Glass slides were dipped in a cleaning (piranha) solution consisting of 70 ml of sulfuric acid and 30 ml of hydrogen peroxide for 30 minutes at 70° C. This was followed by sonication in the same solution for 10 minutes.
Deposition of the Film onto the Glass Substrate
2 ml of a chloroform solution containing the TRCDA monomer and DMPC (in a concentration of 60 mM) were placed on the glass substrate which was then rotated at 1500 rpm for 45 seconds (Headway Research spin coater) in order to create the homogenous layer. The film-covered glass slides were dried at 50° C. for three hours and subsequently UV-irradiated at 254 nm, using 12 W UV-lamp positioned 5 cm above the glass slide.

Agarose Coating

The agarose coating was prepared and applied onto the spin-dried film according to the description of Example 1.

Example 3

Detecting the Presence of Bacteria in Urine Sample

Into several 2 cc urine samples collected from a healthy man were added aliquots (40 µl) taken from stock solutions that were used for the growth of either *Escherichia coli* (XL1) or *salmonella enterica* serovar typhimurium (1a (CS093)). The number of the bacteria in each aliquot was estimated to be approximately one million.

A glass slide carrying an agarose-coated film prepared according to Example 1 was immersed in the resulting spiked urine sample. The test glass slide was then transferred to an incubator at 27° C. After 4 hours, a clear blue to red color transition was observed.

In contrast, the control glass slides:
i) a glass slide prepared according to Example 1, immersed in a non-spiked urine sample; and
(ii) a glass slide carrying a non-coated film (namely, a film obtained by the omission of the agarose coating step from the procedure of Example 1), immersed in a spiked urine sample, did not display a similar color change. The control glass slide (ii) exhibited a color transition several hours after this effect was observed for the test glass slide.

Example 4

Detecting the Presence of Bacteria in a Platelet Sample

Aliquots (40 µl) taken from stock solutions that were used for the growth of *E. coli* and *salmonella* strains were added into 1 cc solutions extracted from a fresh (less than 2-day old) platelet donation (obtained from the blood bank). The number of the bacteria in each aliquot was estimated to be approximately one million.

A glass slide carrying an agarose-coated film prepared according to Example 1 was contacted with the resulting spiked platelet sample. The test glass slide was then transferred to an incubator at 27° C. After 3 to 4 hours, a clear blue to red color transition was observed.

In contrast, the control glass slides:
i) a glass slide prepared according to Example 1, immersed in a non-spiked platelet sample; and
(ii) a glass slide carrying a non-coated film (namely, a film obtained by the omission of the agarose coating step from the procedure of Example 1), immersed in a non-spiked platelet sample,
did not display a similar color change. Specifically, the color of the film in the control glass slide (i) did not change from blue to red, whereas control glass (ii) exhibited the color transition immediately after it was brought into contact with the non-spiked platelet sample. These observations suggest that the agarose coating is capable of effectively masking color changes induced by the components of the plasma, such that the blue to red color transition observed for the test glass slide following an incubation period of about 3 to 4 hours may be attributed to the presence of the bacteria in the spiked sample.

Example 5

Preparation of Agarose-Coated Film Containing Polydiacetylenes, Lipids and an Antibiotic Agent In this example, the following three bacterial strains were used:
1) *Salmonella* serovar typhimurium 1a (cs093)
2) *Salmonella* serovar typhimurium 1a-Mutant (Kanamycin resistant)
3) *Escherichia coli* MC4100 (streptomycin resistant)

Cell Growth:

*Salmonella* 1a was grown in liquid culture Luria-Bertani (LB—standard medium) over night at 37° C. *E. coli* MC4100 was grown over night at 37° C. in LB medium supplemented streptomycin (10 µg/ml). *Salmonella*-1a mutant was grown over night at 37° C. in LB medium supplemented Kanamycin (40 µg/ml).

Agarose-Coated Film Preparation:

The procedure described in Example 1 was followed to prepare several Agarose-coated films. However, into the LB-Agarose liquid suspension was also added an antibiotic compound [either streptomycin (10 µg/ml) or kanamycin (40 µg/ml)]. The resulting suspension was then used to coat the film. Accordingly, streptomycin-containing and kanamycin-containing agarose-coated films were obtained.

Experiment

All strains were streaked on:
(i) a blue agarose-coated film deposited on a glass slide (the "control glass slide");
(ii) a blue streptomycin-containing agarose-coated film deposited on a glass slide; and
(iii) a blue kanamycin-containing agarose-coated film deposited on a glass slide,
at 35° C. for 4 hours.

The blue to red color transitions were observed only in those agarose-coated films that were used for the growth of strains that were resistant to the antibiotic agent present in the agarose coating.

Example 6

Testing Contaminated Urine

Urine containing bacteria (*Escherichia coli* >10,000 CFU/ml) obtained from a sick person at the Soroka Medical Center (Be'er-Sheva, Israel) was streaked on the surface of a blue agarose-coated film deposited on a glass slide, prepared according to Example 1. Spots in which the blue to red color transitions occurred were visibly detected after 5 hours at 35° C. The control (urine sample from a healthy person, containing no bacteria, streaked on the surface of a blue agarose-coated film deposited on a glass slide, prepared according to Example 1), did not produce the color transitions.

Example 7

Testing Contaminated Blood

Blood containing bacteria (*Klebsiella pneumoniae*) obtained from a sick person at the Soroka Medical Center (Be'er-Sheva, Israel) was streaked on the surface of a blue agarose-coated film deposited on a glass slide, prepared according to Example 1. Spots in which the blue to red color transitions occurred were visibly detected after 3 hours at 35° C. The control (blood sample from a healthy person, containing no bacteria, streaked on the surface of a blue agarose-coated film deposited on a glass slide, prepared according to Example 1), did not produce the color transitions.

The invention claimed is:

1. A method for detecting the presence of an analyte in a sample, comprising:
    contacting the sample to be tested with a film of polydiacetylenes and lipids deposited on a substrate, wherein said film is coated with one or more layers, and wherein at least one of said layers contains materials and nutrients that support the growth of microorganisms, and
    following a suitable incubation period, either observing the color of said coated film or detecting the fluorescence emission thereof,
    wherein a change in said color or a characteristic fluorescence emission indicates the presence of said analyte in the tested sample,
    wherein the analyte is bacteria, and
    wherein the tested sample is a food product.

2. A method for determining the antibiotic resistance of a bacterial strain, which comprises:
    contacting the bacterial strain to be tested with the colorimetric and/or fluorescent detector, wherein the colorimetric and/or fluorescent detector comprises a film of polydiacetylenes and lipids deposited on a substrate, wherein said film is coated with one or more layers, and wherein at least one of said layers contains materials and nutrients that support the growth of microorganisms and further comprises one or more compounds exhibiting antibacterial activity within the coating layer, and
    following a suitable incubation period, either observing the color of said coated film or detecting a fluorescent emission thereof, wherein a change in said color or a characteristic fluorescence emission indicates that said bacterial strain is resistant to said antibiotic agent.

* * * * *